United States Patent [19]

Foster et al.

[11] Patent Number: 5,616,807
[45] Date of Patent: Apr. 1, 1997

[54] PROCESS FOR PREPARING ALKYL ANILINES

[75] Inventors: James A. Foster, Corpus Christi, Tex.; Werner H. Mueller, Charlotte, N.C.; Debra A. Ryan, Corpus Christi, Tex.

[73] Assignee: Hoechst Celanese Corp., Somerville, N.J.

[21] Appl. No.: 442,083

[22] Filed: May 16, 1995

Related U.S. Application Data

[63] Continuation-in-part of Ser. No. 56,554, Apr. 30, 1993, abandoned.

[51] Int. Cl.$^6$ ................................................. C07C 209/26
[52] U.S. Cl. ................................................................. 564/423
[58] Field of Search ................................................. 564/423

[56] References Cited

U.S. PATENT DOCUMENTS

| | | | |
|---|---|---|---|
| 2,298,284 | 10/1942 | Emerson | 260/577 |
| 2,779,789 | 1/1957 | Rosenwald | 260/577 |
| 3,209,030 | 9/1965 | Bicek | 260/574 |
| 3,538,161 | 11/1970 | Dovell | 260/576 |

OTHER PUBLICATIONS

Chem Abstracts., vol. 37, 1450 (1943), Describing U.S. Pat. No. 2,298,284.

Organic Reactions, vol. IV, John & Wiley & Sons, Inc., New York, 1948, pp. 174–255 Chapter 3, "The Preparation Of Amines By Reductive Alkylation".

"Secondary Amines From Nitro Compounds", J. Am. Chem. Soc., vol. 62 (1940), pp. 69–70.

Primary Examiner—Brian M. Burn
Attorney, Agent, or Firm—James L. McGinnis

[57] ABSTRACT

A process for the production of N-alkyl anilines by the concurrent hydrogenation of a nitrobenzene to an aniline and the acylation of the aniline with acyl anhydride takes place on a continuous basis in a stirred tank reactor in which liquid product is continuously withdrawn from the reactor.

29 Claims, No Drawings

PROCESS FOR PREPARING ALKYL ANILINES

This is a continuation-in-part of application Ser. No. 08/056,554 filed on Apr. 30, 1993 (now abandoned).

FIELD OF THE INVENTION

This invention relates to the production of N-alkyl aniline by hydrogenation of nitrobenzene to aniline, and concurrently alkylating the aniline. The invention has particular use in forming N-alkyl aniline by hydrogenation of nitrobenzene and concurrent alkylation of the formed aniline as above described in one step and on a continuous basis.

BACKGROUND OF THE INVENTION

The conventional process for the production of N-alkyl aniline involves the batch scale reduction of nitrobenzene to produce aniline which is then alkylated to produce the corresponding N-alkyl aniline. Typical of the alkylation-reduction processes are those found in U.S. Pat. No. 2,580,284; J. Am. Chem. Soc. 1955,77,4052; J. Am. Chem. Soc. 1956,78,1635; and J. Org. Chem. 1956,21,474. Kinetics and Catalysis, 1982,23(1), 56 reports a 56% yield of secondary amine and a 32% yield of the tertiary amine with a 160 minute reaction time in a batch process for the reaction of nitrobenzene and n-propanal at 45° C. increasing to 98% secondary amine and 0% tertiary amine in 465 minutes at 20° C. Several patents report the exclusive preparation of tertiary amines from the reaction of aldehydes with aniline and hydrogen utilizing a Pt/C catalyst. (see Chem. Abstr. 155 7362m, 71108v, 28878j; 110 59530r; and 109 149060w) The reduction of nitrobenzene to produce aniline involves hydrogenating the nitrobenzene in the presence of catalysts such as platinum, palladium, nickel, noble metal catalysts, or oxides of platinum, palladium, or noble metal catalysts. Gaseous hydrogen is commonly used as a reducing agent. The alkylating agent is usually an aldehyde or alcohol. If the alkylation is carried out with an alkyl alcohol, the product is usually a mixture of the secondary and tertiary amine. If the reaction is carried out with an aldehyde, the intermediate imine is hydrogenated to form, predominately the secondary amine. The reaction medium can be any non-interfering solvent. Preferred solvents include water, alcohols, and water-alcohol mixtures, or other inert medium.

Unfortunately, it has been found that nitro reductions, especially of aromatic compounds involve the sequential reduction of highly reactive and unstable intermediates, including nitroso-, hydrazo-, azo-, and azoxy-compounds. These reactive intermediates can lead to several undesirable by-products, which are often very highly colored. The batch reductions cannot minimize these reactive intermediates. In the batch process, the heat release from the reaction continually changes rendering it difficult to provide accurate temperature control.

It has been known to reduce aromatic nitro compounds on a continuous basis in a stirred tank reactor. However, the use of a stirred tank reactor to conduct a one-step process in which an aniline and the alkylated derivative thereof are formed concurrently on a continuous basis has not been previously suggested in the prior art.

SUMMARY OF THE INVENTION

This invention provides a process for producing N-alkyl aniline comprising, catalytically hydrogenating a nitrobenzene to an aniline and concurrently alkylating the aniline to an N-alkyl aniline by forming an imine from reaction of the formed amine with an aldehyde and reducing the formed imine to a secondary amine on a continuous basis in a well-stirred continuous stirred tank reactor (CSTR) compared to batch hydrogenation, the continuous process affords a high purity product by minimizing the concentration of reaction intermediates which form highly colored by-products. The continuous process is also simpler to operate. Heat release is constant and easily controlled compared to batch reactions where the heat release continually changes. Catalyst activity and selectivity remain high for a longer time (preferably more than one day) in the continuous process in the CSTR as compared with the batch process. The catalyst also remains active and selective when used in a CSTR, even when the feed of reactants and removal of products is stopped and the reactor is allowed to cool for a period of time, followed by re-initiation of the reaction. Conversion of nitrobenzene is high, being at least about 90% and preferably being greater than about 99%.

DETAILED DESCRIPTION OF THE INVENTION

According to the present invention, a nitrobenzene is reduced with gaseous hydrogen in the presence of a hydrogenation catalyst and at least one equivalent of an alkyl aldehyde to produce an N-alkyl aniline. Surprisingly, the reduction of the nitrobenzene can be carried out at room temperature and at relatively low pressures compared with the reactions described in the prior art, but higher pressures and/or temperatures may of course be used. Importantly, the reaction takes place on a continuous basis in a well-stirred continuous stirred tank reactor from which product is continuously removed. The process produces typically a yield of at least 98% of alkyl aniline of excellent quality, purity, color, and appearance.

The nitrobenzenes useful as reagents in this invention include nitrobenzene and derivatives thereof in which one or more aromatic ring hydrogens are replaced with substituents which do not adversely affect the desired concurrent reactions. The term alkyl aldehyde is used to describe the functional group wherein $R^1$ is a member of the group consisting of $C_1$–$C_4$ alkyl although there is no known reason to expect that the higher alkyl compounds will not behave in like manner given the proper reaction conditions.

The process of the present invention can be carried out at room temperature, but higher temperatures between about 50° C. and 175° C. are preferred. Preferably, temperatures between about 60°–100° C. are used. The process may be carried out at a hydrogen pressure between 1 atmosphere to 100 atmospheres. Preferably, pressures of from about 5 atm to 50 atm are used. The amount of catalyst, calculated as actual metal in units of the starting material nitrobenzene, is between 0.05 and 30 wt. %. Excellent results are obtained by using finely divided Raney nickel; palladium metal; palladium on charcoal, silica gel, alumina, kieselguhr, chromium oxide, zirconium oxide, bentonite, asbestos, etc. Raney nickel and Pd/C are preferred catalysts. The catalyst itself may be in the form of pellets, granules, powder, etc. and the metal may be precipitated on the carrier in the form of the metal or compound thereof which is reduced in situ in the presence of hydrogen.

The reactions of the present invention may be carried out in an inert solvent, although no advantage is seen in increasing the volume of the reaction mixture above that required to keep the reaction mixture in solution at the temperature of the reaction. Solvents such as alcohols, ethers, or hydrocarbons and organic acids may be used. The term "inert" is meant to express that the solvent does not react with the starting material, the end product of the reaction, the intermediary aniline, the catalyst, or the alkyl aldehyde used in the reaction. Most conveniently, the alcohol related to the aldehyde is used as a diluent since it does not add any undesirable ingredients to the reaction mixture. The amount of alkyl aldehyde to take part in the reaction is chosen between one equivalent and any reasonable excess thereover. Excellent results are obtained by using 1 to 1.2 equivalents of aldehyde per equivalent of nitrobenzene. Large excesses of aldehyde are to be avoided since they may lead to the dialkylated product.

The reactor which is utilized in the process of the present invention is a well-stirred continuous stirred tank reactor (CSTR), which comprises a tank fitted with one or more impellers to ensure optimal mixing. The CSTR is also equipped with feed tubes for reactants that are in the form of liquids or solutions, a take-off tube for continuous removal of solutions and a tube for the bubbling of hydrogen through the solution. The tank can be baffled to further enhance mixing of the reactants. The contents of the CSTR are thoroughly mixed so that reactants that are fed to the reactor are rapidly mixed with the materials already in the reactor. CSTR's are well-known in the art. They are known to be useful for controlling exothermic reactions, but are not normally used when high conversions are desired. In operation, the nitrobenzene, aldehyde, inert solvent, and catalyst are fed to the reactor. Hydrogen is bubbled in to reduce the nitrobenzene to the aminobenzene and to reduce the imine to the amine. Catalyst slurry concentrations such as Raney nickel typically range from about 1 to 30 wt. % of the reactor contents. The nitrobenzene will typically comprise between about 10 and 40 wt. % of the reactor feed. Higher amounts of the nitrobenzene reduce the amount of the solvent needed in the reactor and the amount which must be recycled. Residence time in the reactor will vary depending upon temperature, the amount of catalyst present as well as the amount of hydrogen pressure and excess of alkyl aldehyde present, but generally will range from about 0.25 to 2 hours with less than 1 hour being typical. Product is continuously drawn from the reactor. The percentage of product in the reactor will vary depending upon the concentration of the nitrobenzene fed to the reactor but it is preferred to maintain the level of product at from about 25 to 40 wt. %. Catalyst which may, inadvertently, be removed from the reactor can be recycled. For example, the Raney nickel catalyst is reusable. The catalyst concentration in the reactor should remain constant. The catalyst can be maintained in the reactor by various means including use of filters in the product liquid stream and, alternatively, by forming a quiescent zone in the reactor by the action of the stirrer, use of baffles or by a similar means in which the product is drawn off from the reactor from within the quiescent zone to minimize withdrawing catalyst.

The following example is only intended to illustrate this invention and are not intended in any way to limit the scope of the invention. All parts and percentages are by weight unless otherwise noted.

EXAMPLE 1

Nitrobenzene at 30 wt. % concentration in isopropanol at 15.2 g./min. and n-propanal at 2.13 g./min. are separately pumped into a 2 L. continuously stirred tank reactor vessel containing 70 g. Raney nickel catalyst held at 60° C. and 700 psig. Product was withdrawn from the vessel at the same rate as the combined input rate providing a residence time of 94 min. in the reactor vessel. The product contained 95% n-propylaniline and 3% di-n-propylaniline at a combined yield of 74% based upon nitrobenzene. Increase of the temperature of the vessel to 120° C. resulted in saturation of the aromatic ring, not in a substantial formation of the tertiary amine.

EXAMPLE 2

The two-liter continuous stirred tank reactor was charged first with a slurry of 70 g of Raney nickel catalyst in water. Isopropanol was then added, followed by nitrobenzene (554 g) as a 21% solution in isopropanol. After hydrogenation began, the concurrent feed of nitrobenzene and propionaldehyde began. The nitrobenzene was fed at a rate of 12.9 g/min. as a 21% solution in isopropanol, and the propionaldehyde was fed at a rate of 2.0–2.3 g/min. The temperature of the reactor was maintained at 60° C., and the reactor pressure was kept at 700 psig by addition of hydrogen. The product stream was removed at the same rate as reactants were added. The residence time of reactants was 111 minutes. The mole ratio of the total amount of propionaldehyde to nitrobenzene that was fed averaged about 1.7 to 1. Samples of the product were analyzed periodically. All of the nitrobenzene was converted to other products. The main products were aniline, N-n-propylaniline, and N,N-di(n-propyl)aniline. Small amounts (much less than 1%) of other products in which the aromatic ring was hydrogenated were sometimes detected. The selectivity of aniline to N-n-propylaniline was in the range of 91% to 94%. This last selectivity is calculated based on the assumption that all substituted anilines are derived from intermediate aniline.

After producing from about 4.7 kg to about 5.3 kg of crude product, reactant feed and removal of crude product was discontinued. The reactor contents were cooled to ambient temperature. On a subsequent day, another continuous synthesis was initiated by heating the reactor contents to the reaction temperature, again starting the reactant feeds, and collecting product. This procedure was repeated twice using the same catalyst over a period of 3 days. The catalyst retained its activity and selectivity for all three days. The hydrogen pressure over three days of continuous runs ranged from 500 to 700 psig, the temperature was maintained at 60° C., and the residence time was in the range 111 to 117 minutes. The feed ratio of propionaldehyde to nitrobenzene varied from about 1.6 to 4.0 over this time. The selectivity of aniline to N-n-propylaniline remained in the range of 91% to 94%. There was a very slight increase in N,N-di-(n-propyl)aniline at the higher concentration of propionaldehyde. Nitrobenzene was always completely (100%) converted to products, mainly aniline and N-(n-propyl)aniline.

EXAMPLE 3

Raney nickel catalyst (70 gms), nitrobenzene (30.2% in isopropanol), propionaldehyde and isopropanol were charged to the reactor without continuous feed of reactants or removal of products for a batch experiment. The mole ratio of propionaldehyde to nitrobenzene was about 1.2. Hydrogenation was carried out in a batch mode at 40°–75° C. under 500 psig of hydrogen pressure for 75 minutes. The feeding of nitrobenzene and propionaldehyde, and the take off of crude product, were then begun to initiate a continuous reaction. The selectivity of aniline to N-n-propylaniline in the continuous run was only about 60%. On a subsequent day, another continuous synthesis was done again using the same catalyst. The aniline selectivities to N-n-propylaniline were still poor (47%–63%). Heavy (i.e. high molecular weight) by-products were also observed. The catalyst appeared to have lost a significant amount of activity and selectivity during the first 75 minutes of use when it was used in a batch mode. It is apparent from the data in Examples 2 and 3 that the catalyst is much more robust and long-lived when used in a continuous mode of operation in a CSTR.

What is claimed is:

1. A process for producing N-alkyl anilines comprising: continuously adding a nitrobenzene, an alkyl aldehyde, and hydrogen to a well-mixed continuous stirred tank reactor, concurrently hydrogenating the nitrobenzene to an aniline and alkylating the aniline in the presence of a hydrogenation catalyst selected from the group consisting of Raney nickel and palladium in said reactor to form an N-alkyl aniline product wherein said product is continuously withdrawn from said reactor at the same rate as the combined rate of addition of the reactants wherein the conversion of said nitrobenzene is at least about 90%.

2. The process of claim 1 wherein said alkyl aldehyde is added at a molar rate ranging from about an equal amount to a 20% excess relative to said nitrobenzene.

3. The process of claim 1 wherein said continuous stirred tank reactor is maintained at a temperature of from about 50° to 175° C.

4. The process of claim 3 wherein said continuous stirred tank reactor is maintained at a temperature of from between about 60° to 100° C.

5. The process of claim 1 wherein said nitrobenzene is hydrogenated under a hydrogen pressure of from about 1 atmosphere to 100 atmospheres.

6. The process of claim 5 wherein said nitrobenzene is hydrogenated under a hydrogen pressure of from about 5 atm to 50 atm.

7. The process of claim 1 wherein said hydrogenation catalyst is palladium.

8. The process of claim 1 wherein said hydrogenation catalyst is Raney nickel.

9. The process of claim 1 wherein said nitrobenzene is fed to said reactor dissolved in a solvent.

10. The process of claim 1 wherein said product is withdrawn from said reactor in the form of a liquid.

11. The process of claim 1 wherein the residence time of reactants in the reactor ranges from about 0.25 to 2 hours.

12. The process of claim 10 wherein a solid product is crystallized from said liquid product leaving said reactor and the liquid which remains from said crystallization is recycled to said reactor.

13. The process of claim 1 wherein said alkyl aldehyde has a structural formula of RCHO wherein R is a $C_1$–$C_4$ alkyl.

14. The process of claim 1 wherein said nitrobenzene is selected from the group consisting of nitrobenzene and substituted derivatives thereof.

15. The process of claim 1 wherein said nitrobenzene is nitrobenzene and said alkyl aldehyde is propanal.

16. The process of claim 15 wherein said aldehyde is added at a molar rate ranging from about an equal amount to a 20% excess relative to said nitrobenzene.

17. The process of claim 15 wherein said continuous stirred tank reactor is maintained at a temperature of from about 50° to 175° C.

18. The process of claim 15 wherein said nitrobenzene is hydrogenated under a hydrogen pressure of from about 1 atmosphere to 100 atmospheres.

19. The process of claim 18 wherein said nitrobenzene is hydrogenated under a hydrogen pressure of from about 5 atm to 50 atm.

20. The process of claim 15 wherein said hydrogenation catalyst is Raney nickel.

21. The process of claim 15 wherein said nitrobenzene is fed to said reactor dissolved in a solvent.

22. The process of claim 21 wherein said solvent is an alcohol.

23. The process of claim 15 wherein said product is withdrawn from said reactor in the form of a liquid.

24. The process of claim 15 wherein the residence time of reactants in the reactor ranges from about 0.5 to 2 hours.

25. The process of claim 1 wherein said hydrogenation catalyst is Raney nickel and said continuous stirred tank reactor is maintained at a temperature of from about 50° to 175° C.

26. The process of claim 25 wherein said nitrobenzene is hydrogenated under a hydrogen pressure of from about 5 atm to 50 atm.

27. The process of claim 26 wherein said nitrobenzene is nitrobenzene and said alkyl aldehyde has a structural formula of RCHO wherein R is a $C_1$–$C_4$ alkyl.

28. The process of claim 27 wherein said aldehyde is propanal.

29. The process of claim 1, wherein the conversion of said nitrobenzene is at least about 99%.

* * * * *